(12) United States Patent
Schmidt

(10) Patent No.: US 7,926,327 B2
(45) Date of Patent: Apr. 19, 2011

(54) APPARATUS FOR DETERMINING THE FILTERABILITY OF FLUIDS, IN PARTICULAR OF TRANSMISSION OILS

(75) Inventor: Armin Schmidt, Illingen (DE)

(73) Assignee: Hydac Filtertechnik GmbH, Sulzbach/Saar (DE)

( * ) Notice: Subject to any disclaimer, the term of this patent is extended or adjusted under 35 U.S.C. 154(b) by 321 days.

(21) Appl. No.: 11/992,852

(22) PCT Filed: Aug. 23, 2006

(86) PCT No.: PCT/EP2006/008265
§ 371 (c)(1),
(2), (4) Date: Mar. 31, 2008

(87) PCT Pub. No.: WO2007/054146
PCT Pub. Date: May 18, 2007

(65) Prior Publication Data
US 2009/0229383 A1    Sep. 17, 2009

(30) Foreign Application Priority Data

Nov. 7, 2005   (DE) .......................... 10 2005 053 417

(51) Int. Cl.
*G01N 37/00*      (2006.01)

(52) U.S. Cl. ....................................................... 73/60.11
(58) Field of Classification Search .................. 73/60.11
See application file for complete search history.

(56) References Cited

U.S. PATENT DOCUMENTS 3,098,359 A * 7/1963 Yarmak et al. .................. 60/452
2005/0172698 A1* 8/2005 Cummings et al. .......... 73/19.01

FOREIGN PATENT DOCUMENTS

DE          198 31 946         2/2000
WO    WO 2004/038386 A2      5/2004

* cited by examiner

*Primary Examiner* — Hezron Williams
*Assistant Examiner* — Nathaniel Kolb
(74) *Attorney, Agent, or Firm* — Roylance, Abrams, Berdo & Goodman, LLP

(57) ABSTRACT

An apparatus for determining the filterability of fluids, in particular of transmission oils, has a test filter device (21) through which a sample amount of the fluid can flow, and a line system which forms a circulation circuit (1) for the fluid. The line system includes a foam tester (3) receiving the sample amount of the fluid. A circulating pump (23) removes fluid from the sample amount situated in the foam tester (3) and conveys it through the filter device (21) and back to the foam tester (3).

4 Claims, 2 Drawing Sheets

APPARATUS FOR DETERMINING THE FILTERABILITY OF FLUIDS, IN PARTICULAR OF TRANSMISSION OILS

FIELD OF THE INVENTION

The present invention relates to an apparatus for determining the filterability of fluids, in particular of transmission oils, having a test filter through which a sample amount of the fluid can flow.

BACKGROUND OF THE INVENTION

To monitor and maintain the condition of technical systems in which fluids are involved as system components, it must be absolutely ensured that the fluids, for example, when they are used as lubricants, maintain the required performance characteristics in the course of operation. Thus, for example, in transmission oils routed through a cooler and a filter as they pass through systems of circulating lubrication, it is necessary to carry out testing of the filterability of the pertinent oils. Conventionally, for this purpose a sample amount of the oil is routed through a test filter, preferably such that a plurality of successive passages of the oil through the filter media is undertaken, that therefore a number of filtration cycles are carried out. This system also permits determination of the compatibilities between the given types of oil and the filter media. In addition, in this way filter passage and material compatibility between the oil and filter, especially with respect to additives, such as, for example, anti-foam and wear protection (EP/AW), can be tested. Furthermore, the effect of filtration on foam formation can be checked.

However, there is the danger that for oils provided with an anti-foam additive package which does not have sufficient stability in operation, after a longer filtration interval the concentration of the anti-foam additive decreases so that intensified, in some cases harmful, foaming of the oil occurs. Therefore it is necessary to check the oil for foaming behavior after a corresponding number of filtration cycles.

SUMMARY OF THE INVENTION

An object of the present invention is to provide a device for determining the filterability of fluids, in particular transmission fluids, enabling checking of their foaming behavior.

In past tests of filterability, the foaming behavior was determined separately from the actual filtration cycles by removing secondary samples which were studied separately for foaming behavior from the filtration test bench after completion of the corresponding number of filtration cycles. According to the present invention, the foam test is integrated directly into the filtration test bench. A series of disadvantages is eliminated in this way.

While in the past the fluid volume in the filtration test bench changed due to removal of a comparatively large amount of the secondary sample, which had a change of the test conditions for the sample, volumes and test conditions thus now remain the same. One exception to this is minor sample removal for optional laboratory studies, such as, for example, special forms of emission spectroscopy. This removal does not result in any time loss for removal of the secondary sample, transport, the foam test and return of the secondary sample to the filtration test bench. Moreover, there is no danger that external effects (fouling, water and the like) in the handling of the secondary sample could constitute an error source for sensitive test runs.

For the device according to the present invention, a foam tester is especially well-suited which has a test housing holding the sample amount of fluid and containing a foamer causing mixing of the fluid with air. These foam testers are available, for example, under the commercial name Flender-Schaumtest [Flender foam test] (A. Friedr. Flender GmbH).

Preferably, the line system of the circulation circuit has a return line leading from the filter to the test housing of the foam tester and feeding the fluid below the liquid level of the sample amount into the test housing. This arrangement avoids foaming by the backflow of the recirculated oil emerging from the filter in the operating phases between the actual foam test, that is, in the time intervals of shutdown of the gear pair used as the foamer.

Preferably, the test filter is a membrane filter with one or multiple filter layers. The filter medium preferably corresponds to the filter material, as is used in a technical systems (for example, the transmission of a wind power plant) with a condition to be monitored by the device according to the present invention. Alternatively, filter elements folded into a star or bag filters and comparable filter arrangements can be used.

Other objects, advantages and salient features of the present invention will become apparent from the following detailed description, which, taken in conjunction with the annexed drawings, discloses a preferred embodiment of the present invention.

BRIEF DESCRIPTION OF THE DRAWINGS

Referring to the drawings which form a part of this disclosure.

DETAILED DESCRIPTION OF THE INVENTION

Figure 1:
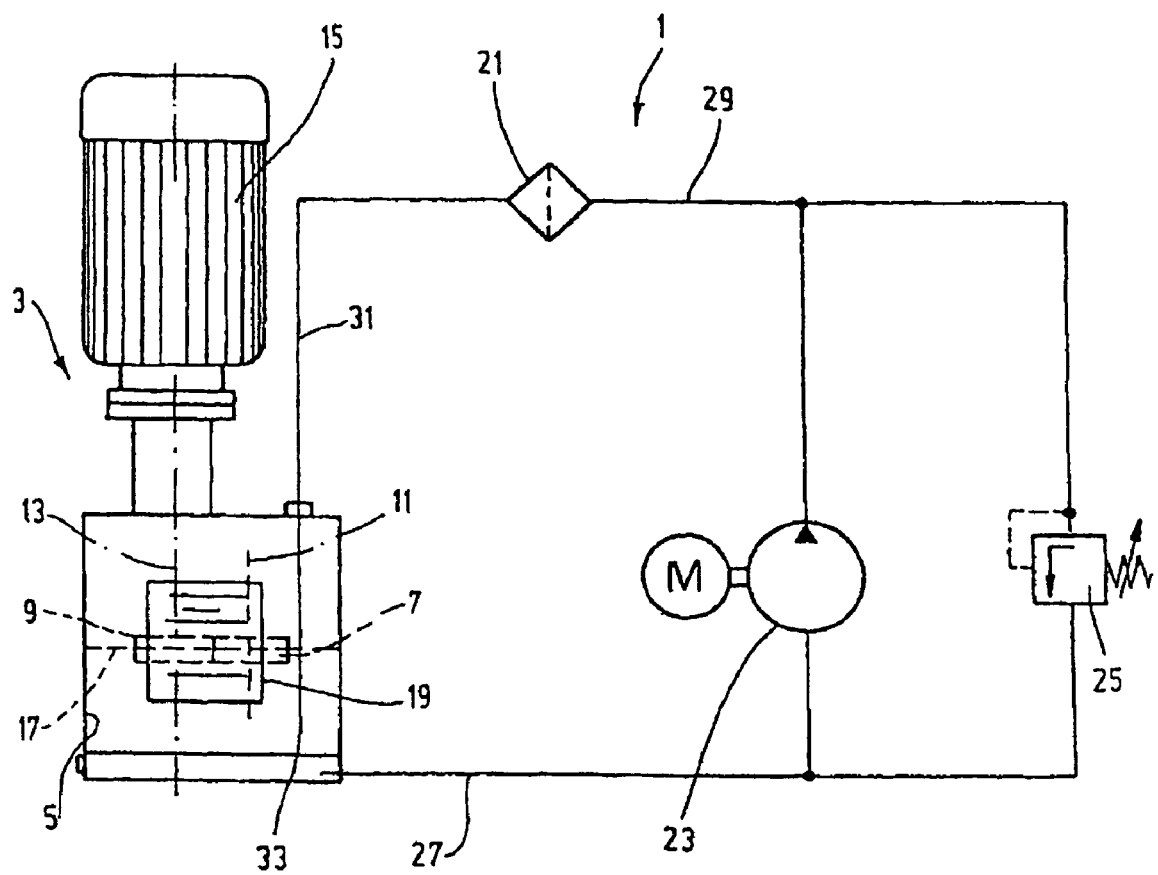
FIG. 1 is a schematic diagram of a device for determining the filterability of fluids according to one exemplary embodiment of the present invention, with a Flender foam tester shown in a side view and a circulation circuit for a fluid to be tested for filterability being shown as a block diagram.

In the exemplary embodiment of the device according to the present invention shown in FIG. 1, a circulation circuit 1 for a fluid to be tested is illustrated. The operation of the device is explained below using the example of testing a fluid in the form of a transmission oil for the transmission of a wind power plant. The circulation circuit 1 integrates a commercial Flender foam tester 3 having a test housing 5 with an interior dimensioned for holding the desired sample amount of the oil to be tested, in this example one liter. In the test housing there is a gear pair as the foamer with intermeshing gears 7 and 9 on vertical axles 11 and 13. The axle 13 forms a drive shaft driven by an electric motor 15 for the gear 9.

As can be recognized through a viewing window 19 in the test housing 5, the gears 7 and 9 are located at a vertical level in which they are halfway immersed in the fluid level 17, so that the rotary motion of the gears 7 and 9 causes mixing of the oil and air.

As other components, the circulation circuit 1 into which the foam tester is integrated has a test filter 21, a circulation pump 23 in the form of an electric motor-drive geared pump, and a pressure limitation valve 25 connected next to the circulation pump 23. The intake side of the circulation pump 23 is connected via a line 27 to the interior of the test housing 5 of the foam tester 3 such that the circulation pump 23 removes fluid from the bottom area of the test housing 5. The pressure side of the pump 23 is connected via a pressure line 29 to the inlet side of the filter 21 having an output side connected in turn to the test housing 5 of the foam tester 3 via a return line 31. The feed opening or mouth 33 of the return line 31, as seen from FIG. 1, is located underneath the fluid level 17 in the test housing 5. Instead of the indicated geared pump, other drive devices for the fluid can also be used.

To test the filterability of the pertinent fluid, the test housing 5 is filled with a sample amount of the fluid to be tested, for example, with transmission oil in an amount (for example, approximately one liter) such that after filling the circulation circuit 1 (lines, pump, filter) the gears 7 and 9 are halfway immersed in the fluid level 7. Before carrying out a corresponding number of filtration cycles, i.e., before circulating the added "fresh oil", by operating the foam tester 3, the original foaming behavior is determined. On a scale division on the viewing window 19, the percentage volume change is determined which is established following an operation-specific waiting time after carrying out the foam test.

A given number of filtration cycles is carried out by operating the circulation pump 23 in the circulation circuit. A cycle is defined as the time required for the test oil to be conveyed once through the test filter 21, viewed statistically. The cycle duration can be computed as the quotient of the fluid volume and the volumetric flow.

After carrying out the desired number of filtration cycles, for example, 100 cycles, the circulation process is interrupted, and a foam test is carried out to determine the change of the foaming behavior. To ascertain how the foaming behavior changes after a still longer operating time, i.e., after completing a large number of filtration processes, a larger number of filtration cycles is carried out, after which the foam tester 3 is restarted to determine the foaming behavior which the test oil exhibits after a longer operating time.

Figure 2:
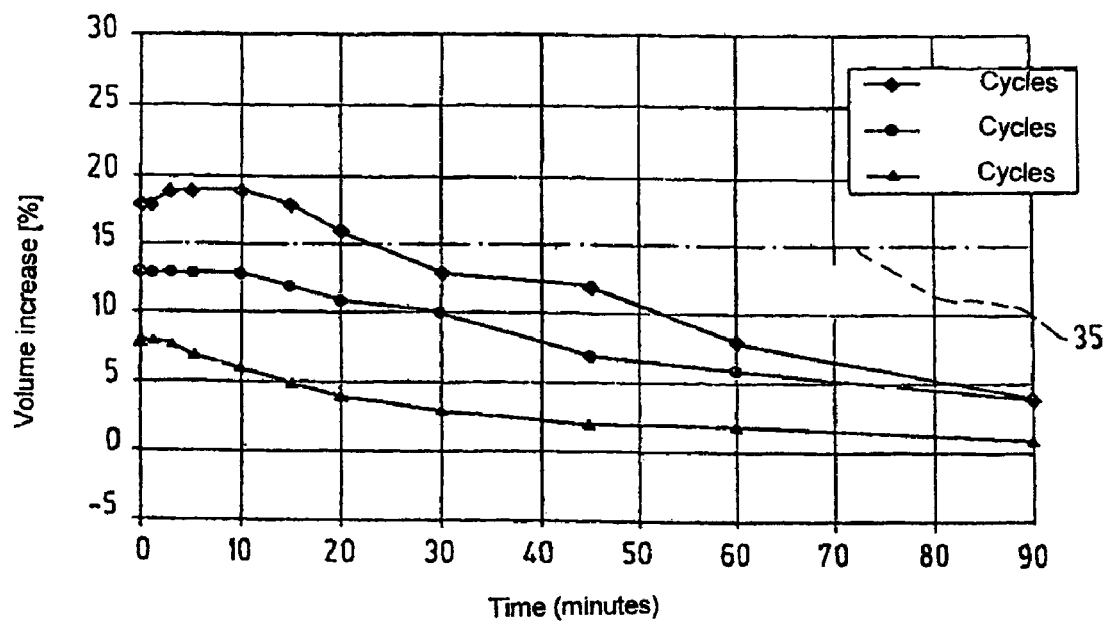
FIGS. 2 and 3 show diagrams in which the results of the testing of two transmission oils carried out with the device according to an exemplary embodiment of the present invention are shown.

FIG. 2 shows the test results determined in the testing of a transmission oil using the percentage volume increase caused by foaming of the test oil. Depending on the kind of oil and the oil category, for example, a volume increase of 15% can be regarded as the highest allowable boundary value.

This boundary value is shown in FIG. 2 by the dot-dash line 35. As is illustrated in FIG. 2 by the lower curve, the test oil before carrying out the filtration cycles has an initial foaming behavior which is far below the boundary value indicated with line 35. As the middle curve shows, foreign behavior can still be assumed even after carrying out a plurality of cycles. This test oil for a longer operating interval, see the upper curve, however, has unsatisfactory foaming behavior, according to a volume increase of more than 15%. The testing of these kinds of oils has thus shown that the test oil contains an insufficiently stable anti-foam additive package. A further variable can also be dictated by temperature control.

Figure 3:
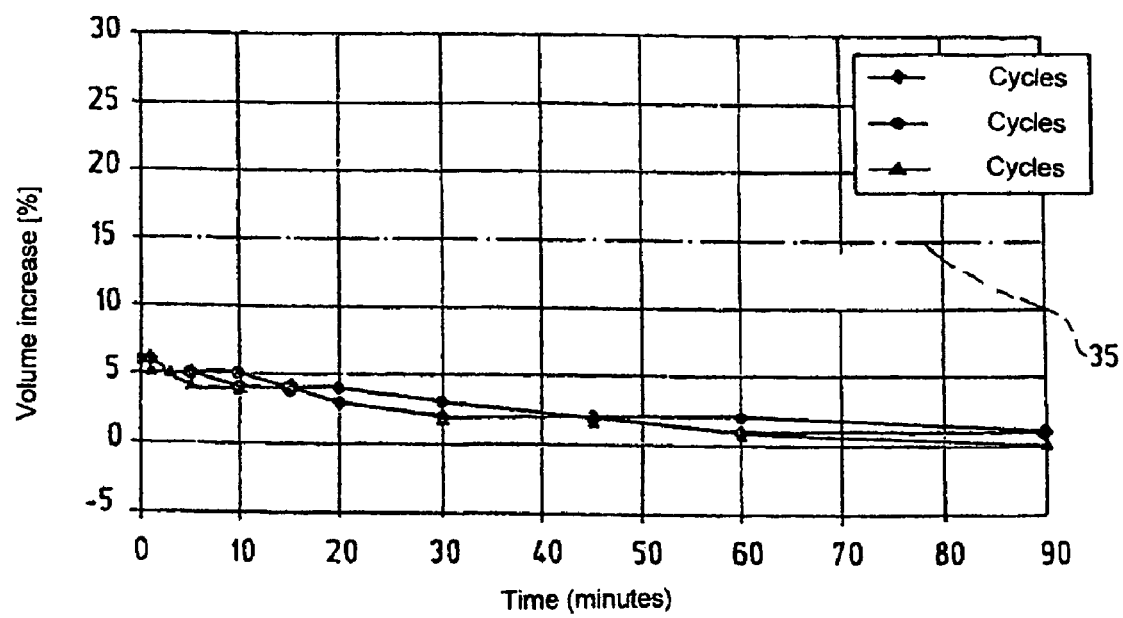

Conversely, FIG. 3 shows the test results for a type of oil in which the additives which suppress foaming exhibit unobjectionable operating behavior. All curves (for the start of testing, for a few cycles and for a great many cycles) extend far below the boundary value of the 15% volume increase by foaming which is indicated by line 35. As shown by the respective upper curve for a plurality of cycles, this type of oil has good operating behavior even for a longer operating interval, i.e., filterability is not adversely affected by the anti-foam additives settling on the surface of the filter material. This result shows a decrease in the concentration of these additives, and thus, excess foam formation. The cycles shown in FIGS. 2 and 3 relative to the triangle symbol used relate to the start of the test; the square symbol relates to the end of the test; and the circular or point indicate an instant between the start of the test and the end of the test.

The filter 21 preferably can have round filter elements in a pressure filter holder. Preferably, filter rounds of the same filter material are used as in the analogous technical system, the condition of which is to be monitored. Instead of the round filter elements, folded filter media, bag filters, or the like can be used. Furthermore, it is possible to use the foam tester or the foam test device as an oil tank for the entire device. With the device according to the present invention, an easily manageable measurement process is specified to draw a conclusion about the filterability of media.

While one embodiment has been chosen to illustrate the invention, it will be understood by those skilled in the art that various changes and modifications can be made therein without departing from the scope of the invention as defined in the appended claims.

What is claimed is:

1. An apparatus for determining filterability of fluids, comprising:
    a line system forming a circulation circuit for the fluid;
    a test filter through which a sample amount of fluid can flow in said circulation circuit;
    a foam tester in said circulation circuit, said foam tester having a test housing holding the sample amount of the fluid and a foamer for mixing the fluid with air, said foamer including a drivable meshing gear pair partially immersed in a liquid level of the fluid in said test housing;
    a circulation pump in said circulation circuit removing fluid from the sample amount located in said foam tester and conveying the fluid from the sample amount through said filter and back to said foam tester; and
    a return line in said circulation circuit leading from said test filter to said test housing of said foam tester and having a feed opening located below the liquid level of the sample amount in said test housing.

2. An apparatus according to claim 1 wherein said test filter is a membrane filter with at least one filter layer.

3. An apparatus according to claim 2 wherein said test filter contains filter rounds in a pressure filter holder.

4. An apparatus according to claim 1 wherein the fluid is transmission oil.

* * * * *